United States Patent
Kondadadi et al.

(10) Patent No.: US 11,152,084 B2
(45) Date of Patent: Oct. 19, 2021

(54) MEDICAL REPORT CODING WITH ACRONYM/ABBREVIATION DISAMBIGUATION

(71) Applicant: Nuance Communications, Inc., Burlington, MA (US)

(72) Inventors: Ravi Kondadadi, Rosemount, MN (US); Girija Yegnanarayanan, Raleigh, NC (US); Brian William Delaney, Bolton, MA (US); John Ortega, Floral Park, NY (US)

(73) Assignee: Nuance Communications, Inc., Burlington, MA (US)

( * ) Notice: Subject to any disclaimer, the term of this patent is extended or adjusted under 35 U.S.C. 154(b) by 386 days.

(21) Appl. No.: 15/045,167

(22) Filed: Feb. 16, 2016

(65) Prior Publication Data
US 2017/0199963 A1    Jul. 13, 2017

Related U.S. Application Data

(60) Provisional application No. 62/278,206, filed on Jan. 13, 2016.

(51) Int. Cl.
*G16H 10/60* (2018.01)
*G16H 15/00* (2018.01)
(Continued)

(52) U.S. Cl.
CPC .............. *G16H 10/60* (2018.01); *G06F 19/00* (2013.01); *G06N 20/00* (2019.01); *G16H 15/00* (2018.01); *G06Q 10/10* (2013.01)

(58) Field of Classification Search
CPC ........ G16H 10/60; G16H 15/00; G06F 19/30; G06F 19/32; G06F 19/34; G06F 19/328;
(Continued)

(56) References Cited

U.S. PATENT DOCUMENTS

| | | |
|---|---|---|
| 4,696,039 A | 9/1987 | Doddington |
| 5,031,113 A | 7/1991 | Hollerbauer |

(Continued)

FOREIGN PATENT DOCUMENTS

| | | | |
|---|---|---|---|
| DE | 19533541 C1 | 3/1997 | |
| WO | WO 98/19253 A1 | 5/1998 | |
| WO | WO-9819253 A1 * | 5/1998 | ............. G16H 10/60 |

OTHER PUBLICATIONS

Taira et al., "Automatic Structuring of Radiology Free-Text Reports", 2001, infoRAD, 21:237-45. (Year: 2001).*

(Continued)

*Primary Examiner* — Elaine Gort
*Assistant Examiner* — Amanda R. Covington
(74) *Attorney, Agent, or Firm* — Wolf, Greenfield & Sacks, P.C.

(57) ABSTRACT

Techniques for coding a medical report include identifying an acronym or abbreviation in the medical report, and a plurality of phrases not explicitly included in the medical report that are possible expanded forms of the acronym or abbreviation in the medical report. From the plurality of phrases, a most likely expanded form of the acronym or abbreviation may be selected by applying to the medical report a statistical acronym/abbreviation expansion model trained on a corpus of medical reports. By applying to the medical report with the expanded acronym or abbreviation one or more statistical fact extraction models, a clinical fact may be extracted from the medical report based at least in part on the most likely expanded form of the acronym or abbreviation in the medical report, and a corresponding medical taxonomy code may be assigned to the extracted clinical fact from the medical report.

22 Claims, 8 Drawing Sheets

(51) Int. Cl.
*G06N 20/00* (2019.01)
*G06F 19/00* (2018.01)
*G06Q 10/10* (2012.01)

(58) Field of Classification Search
CPC ........ G06F 19/00; G06Q 10/10; G06Q 40/08; G06Q 50/22; G06Q 50/24
See application file for complete search history.

(56) References Cited

U.S. PATENT DOCUMENTS

| | | | |
|---|---|---|---|
| 5,051,924 | A | 9/1991 | Bergeron et al. |
| 5,680,511 | A | 10/1997 | Baker et al. |
| 5,758,322 | A | 5/1998 | Rongley |
| 5,787,394 | A | 7/1998 | Bahl et al. |
| 5,909,667 | A | 6/1999 | Leontiades et al. |
| 5,999,896 | A | 12/1999 | Richardson et al. |
| 6,003,002 | A | 12/1999 | Netsch |
| 6,073,101 | A | 6/2000 | Maes |
| 6,173,259 | B1 | 1/2001 | Bijl et al. |
| 6,212,498 | B1 | 4/2001 | Sherwood et al. |
| 6,360,237 | B1 | 3/2002 | Schulz et al. |
| 6,366,882 | B1* | 4/2002 | Bijl ............... G06F 3/16 704/231 |
| 6,418,410 | B1 | 7/2002 | Nassiff et al. |
| 6,434,547 | B1 | 8/2002 | Mishelevich et al. |
| 6,463,413 | B1 | 10/2002 | Applebaum et al. |
| 6,487,530 | B1 | 11/2002 | Lin et al. |
| 6,567,778 | B1 | 5/2003 | Chao Chang et al. |
| 6,813,603 | B1 | 11/2004 | Groner et al. |
| 6,915,254 | B1* | 7/2005 | Heinze ............ G06F 17/27 704/9 |
| 7,233,938 | B2* | 6/2007 | Cams ............ G06Q 50/22 705/2 |
| 7,383,172 | B1 | 6/2008 | Jamieson |
| 7,493,253 | B1 | 2/2009 | Ceusters et al. |
| 7,610,192 | B1* | 10/2009 | Jamieson ........ G06F 17/2229 704/9 |
| 8,326,653 | B2* | 12/2012 | Gottlieb ........ G06F 19/328 705/4 |
| 8,515,782 | B2* | 8/2013 | Walker ........ G06F 19/328 705/3 |
| 8,589,149 | B2* | 11/2013 | Cecil ............ G06F 3/0237 345/168 |
| 8,788,289 | B2* | 7/2014 | Flanagan ........ G06Q 10/10 705/3 |
| 8,943,437 | B2* | 1/2015 | Meurs ............ H04L 12/1859 715/816 |
| 9,317,601 | B2* | 4/2016 | Dozier ............ G06F 17/2785 |
| 9,478,218 | B2 | 10/2016 | Shu |
| 9,892,734 | B2* | 2/2018 | Koll ............ G06F 17/211 |
| 9,905,229 | B2* | 2/2018 | Montyne ........ G10L 15/26 |
| 9,916,420 | B2* | 3/2018 | Cardoza ........ G16H 10/60 |
| 9,922,385 | B2* | 3/2018 | Yegnanarayanan .... G06Q 10/10 |
| 2003/0088562 | A1* | 5/2003 | Dillon ............ G06F 16/30 |
| 2003/0115083 | A1 | 6/2003 | Masarie, Jr. et al. |
| 2004/0243545 | A1* | 12/2004 | Boone ............ G06F 19/00 |
| 2005/0033574 | A1 | 2/2005 | Kim et al. |
| 2005/0240439 | A1* | 10/2005 | Covit ............ G06Q 10/00 705/2 |
| 2005/0289168 | A1* | 12/2005 | Green ............ G06F 16/951 |
| 2006/0241943 | A1* | 10/2006 | Benja-Athon ....... G06Q 10/10 704/235 |
| 2007/0033026 | A1 | 2/2007 | Bartosik et al. |
| 2007/0156674 | A1* | 7/2007 | Dozier ............ G06F 17/2785 |
| 2007/0208567 | A1 | 9/2007 | Amento et al. |
| 2007/0276649 | A1* | 11/2007 | Schubert ........ G06F 17/2276 704/2 |
| 2008/0004505 | A1* | 1/2008 | Kapit ............ G16H 15/00 600/300 |
| 2008/0243500 | A1* | 10/2008 | Bisani ............ G06F 17/2715 704/235 |
| 2008/0255835 | A1 | 10/2008 | Ollason et al. |
| 2008/0270120 | A1* | 10/2008 | Pestian ............ G06F 17/2785 704/9 |
| 2009/0287678 | A1* | 11/2009 | Brown ............ G06F 17/28 |
| 2010/0049756 | A1 | 2/2010 | Chemitiganti et al. |
| 2011/0040576 | A1* | 2/2011 | Madan ............ G06Q 10/10 705/3 |
| 2012/0330648 | A1* | 12/2012 | Boguraev ........ G06F 17/2735 704/9 |
| 2013/0297348 | A1* | 11/2013 | Cardoza ........ G16H 10/60 705/3 |
| 2013/0304453 | A9* | 11/2013 | Fritsch ............ G06F 17/2785 704/9 |
| 2014/0297266 | A1* | 10/2014 | Nielson ............ G09B 7/08 704/9 |
| 2015/0379241 | A1* | 12/2015 | Furst ............ G06F 17/2705 705/3 |
| 2018/0081859 | A1* | 3/2018 | Snider ............ G06F 17/21 |

OTHER PUBLICATIONS

Cimiano et al., Learning concept hierarchies from text with a guided hierarchical clustering algorithm. In C. Biemann and G. Paas (eds.), Proceedings of the ICML 2005 Workshop on Learning and Extending Lexical Ontologies with Machine Learning Methods, Bonn, Germany, (2005).

Fan et al., Prismatic: Inducing Knowledge from a Large Scale Lexicalized Relation Resource. Proceedings of the NAACL HLT 2010 First International Workshop on Formalisms and Methodology for Learning by Reading, pp. 122-127, Los Angeles, California, Jun. 2010.

Florian et al., A Statistical Model for Multilingual Entity Detection and Tracking Proceedings of the Human Language Technologies Conference 2004 (HLT-NAACL'04), (2004).

Gomez-Perez et al., An overview of methods and tools for ontology learning from texts. Knowledge Engineering Review 19:3 p. 187-212, 2004.

Joshi et al., A comparative study of supervised learning as applied to acronym expansion in clinical reports. AMIA Annu Symp Proc. 2006:399-403.

Kim et al., Using UMLS lexical resources to disambiguate abbreviations in clinical text. AMIA Annu Symp Proc. 2011;2011:715-22. Epub Oct. 22, 2011.

Pakhomov et al., Abbreviation and acronym disambiguation in clinical discourse. AMIA Annu Symp Proc. 2005:589-93.

Salton et al., A Vector Space Model for Automatic Indexing. Communications of the ACM, vol. 18, No. 11, Nov. 1975.

Welty et al., Large Scale Relation Detection. Proceedings of the NAACL HLT 2010 First International Workshop on Formalisms and Methodology for Learning by Reading, pp. 24-33, Los Angeles, California, Jun. 2010.

Wu et al., A comparative study of current Clinical Natural Language Processing systems on handling abbreviations in discharge summaries. AMIA Annu Symp Proc. 2012:2012:997-1003, Epub Nov. 3, 2012.

Aronow et al., Ad Hoc Classification of Radiology Reports. Journal of the American Medical Informatics Association. 1999;6(5):393-411.

Bateman et al., The Quest for the Last 5%: Interfaces for Correcting Real-Time Speech-Generated Subtitles. Interactive Posters. CHI 2000. 2 pages.

Birnbaum et al., Report: A Voice Password System for Access Security. AT&T Technical Journal. 1986. 7 pages.

Bisani et al., Automatic Editing in a Back-End Speech-to-Text System. Proceedings of ACL-08: HLT. 2008:114-20.

Heng-Hsou et al., An Event-Driven and Ontology-Based Approach for the Delivery and Information Extraction of E-mails. IEEE. 2000. 103-9.

Hewitt et al., Real-Time Speech-Generated Subtitles: Problems and Solutions. ISCA Archive. 6th International Conference on Spoken Language Processing (ICSLP 2000). 2000. 5 pages.

Mendonca et al., Extracting information on pneumonia in infants using natural language processing of radiology reports. Journal of Biomedical Informatics. 2005;38:314-21.

(56) References Cited

OTHER PUBLICATIONS

Naik, Speaker Verification: A Tutorial. IEEE Communications Magazine. 1990:42-8.

Newman et al., Speaker Verifcation Through Large Vocabulary Continuous Speech Recognition. Dragon Systems, Inc. 1996. 4 pages.

Rosenberg, Evaluation of an Automatic Speaker-Verification System Over Telephone Lines. Manuscript received Sep. 9, 1975. The Bell System Technical Journal. 1976;55(6):723-44.

Shvaiko et al., Ontology Matching OM-2008. Papers from the ISWC Workshop. 2008. 271 pages.

Sistrom et al., Managing Predefined Templated and Macros for a Departmental Speech Recognition System Using Common Software. Journal of Digital Imaging. 2001;14(3):131-41.

Soderland et al., Automated Classification of Encounter Notes in a Computer Based Medical Record. MEDINFO 1995 Proceedings. 1995 IMIA. 9 pages.

Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010. 12 pages.

Sonntag et al., RadSpeech's Mobile Dialogue System for Radiologists. IUI'12. 2012. 2 pages.

Suhm, Multimodal Interactive Error Recovery for Non-Conversation Speech User Interfaces. Dissertation. 1998. 292 pages.

Taira et al., Automatic Structuring of Radiology Free-Text Reports. infoRAD. Radiology 2001;21:237-45.

\* cited by examiner

| Patient Name | John Doe | Sex | M | Creation Date | 01-18-2011 |
| Document Type | Discharge Summary | | | | |

Chief complaint: Patient is presenting chest pain and shortness of breath.

Medical history: The patient is hypertensive. He is also obese.

Social history: He smokes one pack per day. Drinks occasionally.

⊞ Problems(:)

Add Fact | Name | Status

⊞ Medications(0)

Add Fact | Name | Status | Schedules

⊞ Allergies(0)

Add Fact | Name | Type | Status | Substance | Reactions

⊞ Social History (:)

Add Alcohol Fact | Add Tobacco Fact

Process | Cancel

Patient Name: John Doe  Sex: M  Creation Date: 01-18-2011
Document Type: Discharge Summary Problems  Medications  Allergies  Social History  Procedures  Vital Signs  Hide All Problems(4) — 310

| Add Fact | | |
|---|---|---|
| | Name | Status |
| x | Unspecified Chest Pain | active |
| x | Shortness of Breath | active |
| x | Unspecified Essential Hypertension | history |
| x | Obesity Unspecified | history |

Medications(1) — 320

| Add Fact | | |
|---|---|---|
| | Name | Status | Schedules |
| x | | | None |

Allergies(0) — 330

| Add Fact | | |
|---|---|---|
| | Name | Type | Status |
| | | | |

Chief complaint: Patient is presenting chest pain and shortness of breath.

Medical history: The patient is hypertensive. He is also obese.

Social history: He smokes one pack per day. Drinks occasionally.

Save  Dictate  Complete  Cancel

MEDICAL REPORT CODING WITH ACRONYM/ABBREVIATION DISAMBIGUATION

CROSS-REFERENCE TO RELATED APPLICATIONS

This application claims the benefit under 35 U.S.C. § 119(e) of U.S. Provisional Application No. 62/278,206, filed Jan. 13, 2016, entitled "MEDICAL REPORT CODING WITH ACRONYM/ABBREVIATION DISAMBIGUATION."

BACKGROUND

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

Another modern trend in healthcare management is the importance of medical coding for documentation and billing purposes. In the medical coding process, documented information regarding a patient encounter, such as the patient's diagnoses and clinical procedures performed, is classified according to one or more standardized taxonomies of codes for reporting to various entities such as payment providers (e.g., health insurance companies that reimburse clinicians for their services). In the United States, some such standardized code systems have been adopted by the federal government, which then maintains the code sets and recommends or mandates their use for billing under programs such as Medicare.

For example, the International Classification of Diseases (ICD) numerical coding standard taxonomy, developed from a European standard by the World Health Organization (WHO), was adopted in the U.S. in version ICD-9-CM (Clinically Modified). It is mandated by the Health Insurance Portability and Accountability Act of 1996 (HIPAA) for use in coding patient diagnoses. The Centers for Disease Control (CDC), the National Center for Health Statistics (NCHS), and the Centers for Medicare and Medicaid Services (CMS) are the U.S. government agencies responsible for overseeing all changes and modifications to ICD-9-CM, and a new version ICD-10-CM was adopted in 2015. Whereas ICD-9-CM included both diagnosis and procedure codes, ICD-10-CM includes only diagnosis codes, and procedure codes form a separate code set ICD-10-PCS (Procedure Coding System).

Another example of a standardized code taxonomy adopted by the U.S. government is the Current Procedural Terminology (CPT) code set, which classifies clinical procedures in five-character alphanumeric codes. The CPT code set is owned by the American Medical Association (AMA), and its use is mandated by CMS as part of the Healthcare Common Procedure Coding System (HCPCS). CPT forms HCPCS Level I, and HCPCS Level II adds codes for medical supplies, durable medical goods, non-physician healthcare services, and other healthcare services not represented in CPT. CMS maintains and distributes the HCPCS Level II codes with quarterly updates.

Conventionally, the coding of a patient encounter has been performed by a designated professional, referred to as a "medical coder" or simply "coder," with expert training in medical terminology and documentation as well as the standardized code sets being used and the relevant regulations. The coder would read the available documentation from the patient encounter, such as the clinicians' narrative reports, laboratory and radiology test results, etc., and determine the appropriate codes to assign to the encounter. The coder might make use of a medical coding system, such as a software program running on suitable hardware, that would display the documents from the patient encounter for the coder to read, and allow the coder to manually input the appropriate codes into a set of fields for entry in the record. Once finalized, the set of codes entered for the patient encounter could then be sent to a payment provider (e.g., a government payment provider such as Medicare, or a private health insurance company), which would typically determine the level of reimbursement for the encounter according to the particular codes that were entered. For example, the ICD code for a particular patient diagnosis might be deemed by the payment provider to warrant a particular reimbursement level for a particular procedure authorized as treatment for that diagnosis.

SUMMARY

One type of embodiment is directed to a method of coding a medical report, the method comprising: identifying an acronym or abbreviation in the medical report, and a plurality of phrases not explicitly included in the medical report that are possible expanded forms of the acronym or abbreviation in the medical report; selecting, from the plurality of phrases, a most likely expanded form of the acronym or abbreviation in the medical report, by applying to the medical report a statistical acronym/abbreviation expansion model trained on a corpus of medical reports and implemented by at least one processor executing stored instructions; extracting a clinical fact from the medical report based at least in part on the most likely expanded form of the acronym or abbreviation in the medical report, by applying to the medical report with the expanded acronym or abbreviation one or more statistical fact extraction models implemented by the at least one processor; and assigning a corresponding medical taxonomy code to the extracted clinical fact from the medical report.

Another type of embodiment is directed to a system comprising at least one processor and at least one storage medium storing processor-executable instructions that, when executed by the at least one processor, perform a method of coding a medical report, the method comprising: identifying an acronym or abbreviation in the medical report, and a plurality of phrases not explicitly included in the medical report that are possible expanded forms of the acronym or abbreviation in the medical report; selecting, from the plurality of phrases, a most likely expanded form of the acronym or abbreviation in the medical report, by applying to the medical report a statistical acronym/abbreviation expansion model trained on a corpus of medical reports; extracting a clinical fact from the medical report based at least in part on the most likely expanded form of the acronym or abbreviation in the medical report, by applying to the medical report with the expanded acronym or abbreviation one or more statistical fact extraction models; and assigning a corresponding medical taxonomy code to the extracted clinical fact from the medical report.

Another type of embodiment is directed to at least one non-transitory computer-readable storage medium storing computer-executable instructions that, when executed, perform a method of coding a medical report, the method comprising: identifying an acronym or abbreviation in the medical report, and a plurality of phrases not explicitly included in the medical report that are possible expanded forms of the acronym or abbreviation in the medical report; selecting, from the plurality of phrases, a most likely expanded form of the acronym or abbreviation in the medical report, by applying to the medical report a statistical acronym/abbreviation expansion model trained on a corpus of medical reports; extracting a clinical fact from the medical report based at least in part on the most likely expanded form of the acronym or abbreviation in the medical report, by applying to the medical report with the expanded acronym or abbreviation one or more statistical fact extraction models; and assigning a corresponding medical taxonomy code to the extracted clinical fact from the medical report.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a screenshot illustrating an exemplary graphical user interface for a medical fact review system in accordance with some embodiments;

FIGS. 3A and 3B are screenshots illustrating an exemplary display of medical facts in a user interface in accordance with some embodiments;

FIG. 4 is a screenshot illustrating an exemplary display of linkage between text and a clinical fact in accordance with some embodiments;

FIG. 5 is a screenshot illustrating an exemplary interface for entering a clinical fact in accordance with some embodiments;

DETAILED DESCRIPTION

Figure 1:
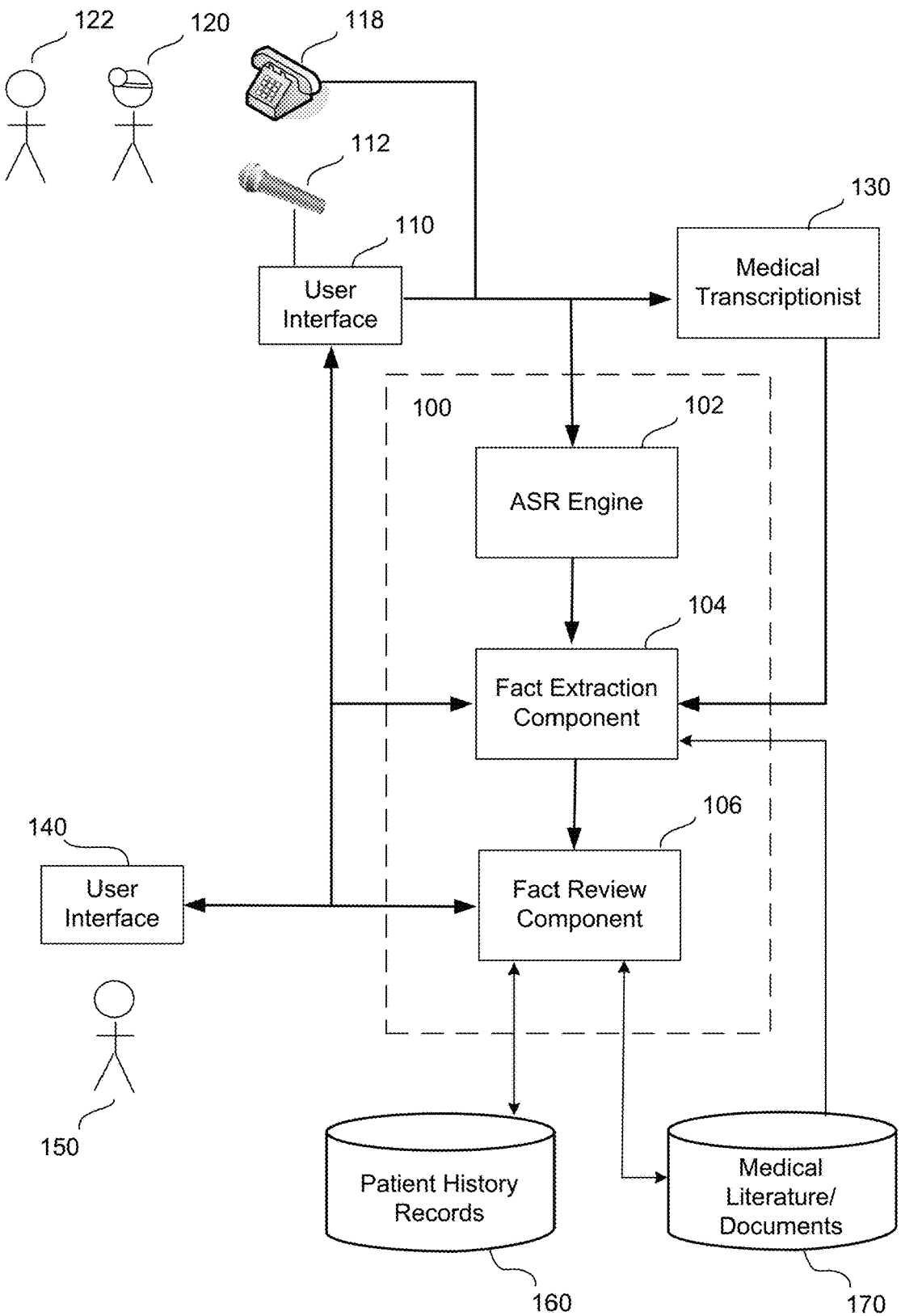
FIG. 1 is a block diagram of an exemplary operating environment for a system in accordance with some embodiments.
Figure 6:
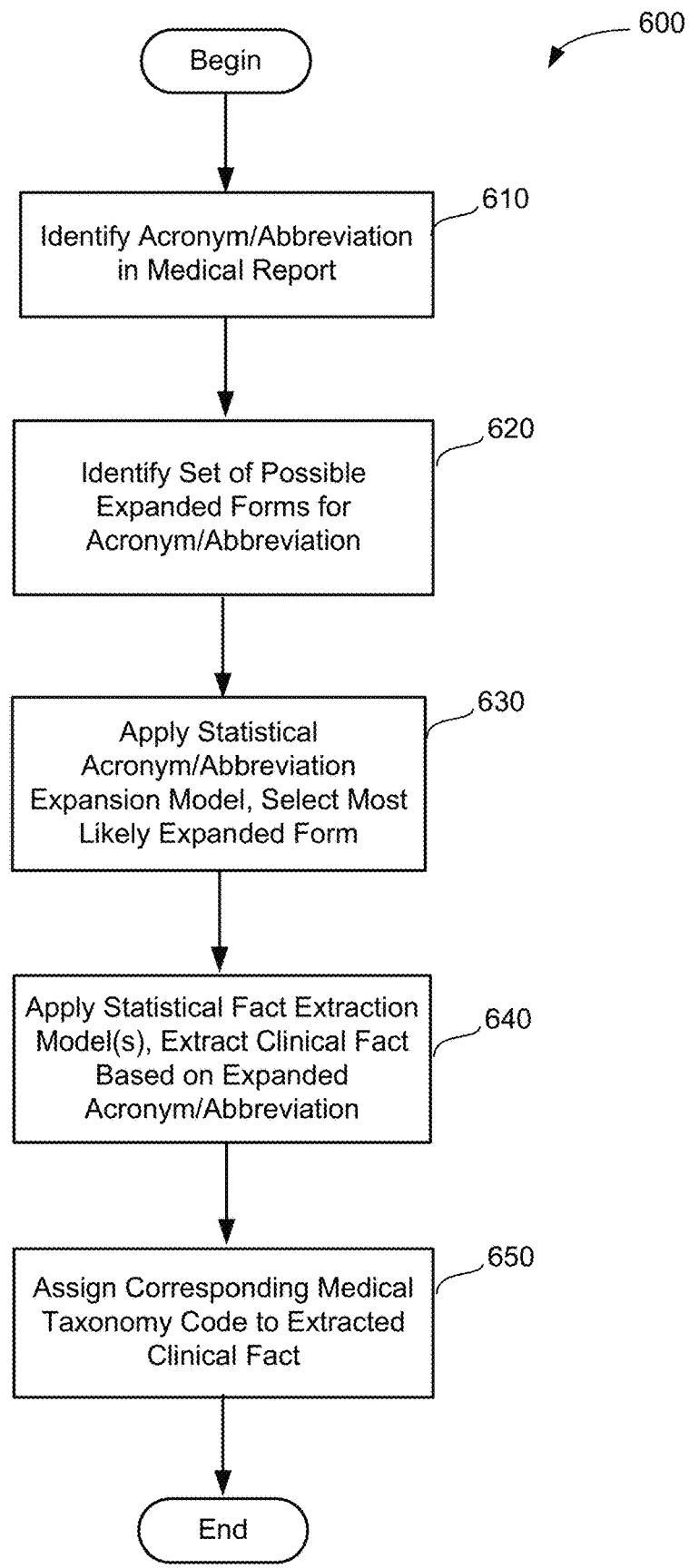
FIG. 6 is a flowchart illustrating an exemplary method of coding a medical report in accordance with some embodiments.

An Electronic Health Record (EHR), or electronic medical record (EMR), is a digitally stored collection of health information that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard taxonomy. For example, "acute myocardial infarction" may be represented in an EHR as "ICD-9 410", where 410 is the code number for "acute myocardial infarction" according to the ninth edition of the ICD standard. Another standard taxonomy often used to define a set of normalized terms for EHRs is the SNOMED CT (Systematized Nomenclature of Medicine Clinical Terms) taxonomy of codes, maintained and distributed by the International Health Terminology Standards Development Organisation. In an EHR using the SNOMED CT code set, "acute myocardial infarction" may be represented as SNOMED CT code 57054005.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

The inventors have recognized, however, that while some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner. In some embodiments, medical documentation may be provided in reports that contain a mix of narrative and structured information, and medical facts may be extracted automatically from both narrative and structured portions of a document, with or without prior designation of the locations of boundaries between structured and unstructured portions.

Automatic extraction of medical facts (e.g., clinical facts) from a free-form narration or other portion of medical documentation may be performed in any suitable way using any suitable technique(s) in some embodiments. Examples of suitable automatic fact extraction techniques are described below. In some embodiments, pre-processing may be performed on a free-form narration prior to performing automatic fact extraction, to determine the sequence of words represented by the free-form narration. Such pre-processing may also be performed in any suitable way using any suitable technique(s) in some embodiments. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as embodiments are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as embodiments are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as embodiments are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. § 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as embodiments are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form; exemplary implementations for a fact extraction component are described in detail below.

The inventors have recognized and appreciated that the automatic extraction of medical facts (e.g., clinical facts) directly from a free-form narration of a patient encounter provided by a clinician, and/or from mixed structured and unstructured documents, may create the opportunity for numerous enhancements to processes involved in medical documentation in healthcare institutions. Some such enhancements may help make it possible for a clinician to efficiently oversee a process involving deriving any one or combination of updated patient records, billing information, ordering information, quality of care assurances, decision support, etc., directly from a free-form narration in a single interactive session with a medical fact review system.

In some embodiments, automatic extraction of clinical facts from a textual representation of a clinician's free-form narration (e.g., from a text narrative) of a patient encounter may be enhanced by re-formatting the text narrative to facilitate the automatic extraction of the clinical facts. For example, in some embodiments a fact extraction component that performs the automatic fact extraction may make use of linguistic knowledge that has some dependency on accurate placement of sentence boundaries in the text narrative. Accordingly, in some embodiments, the fact extraction may be enhanced by adding, removing and/or correcting sentence boundaries in the text narrative to comply with the linguistic structure expected by the fact extraction component. Examples of ways in which sentence boundary pre-processing can be implemented are described below. In another example, automatic fact extraction may be enhanced by normalizing section headings in the text narrative to comply with standard section headings used by the healthcare institution for which the clinical documentation is being performed.

The inventors have also recognized and appreciated that acronyms and abbreviations are widely and frequently used by clinicians in writing or dictating medical reports, and can create significant difficulties for an automatic fact extraction system. Often, the same acronym or abbreviation can stand for more than one different medical term, such that an automatic fact extraction system may mistakenly extract a clinical fact related to one possible expanded form of an acronym or abbreviation in a medical report text, when a different term was actually intended by the acronym or abbreviation. For example, the initials "CP" in a medical report could stand for any of numerous different clinically relevant phrases, such as "chest pain," "cardiac pacing," "chicken pox," "cleft palate," "cerebral palsy," "child psychiatry," "crystalline penicillin," "creatinine phosphate," "current practice," and others. The same initials could even stand for other phrases that are not clinical terms, such as the name of a signing clinician whose initials are "CP." The inventors have recognized that the presence of acronyms or abbreviations in place of the expanded forms of terms in medical reports, whether in structured portions or unstructured narrative portions, can present a stumbling block to an automatic fact extraction system in determining which clinical fact accurately represents the intended meaning of a portion of a clinician's text narrative or mixed report that includes an ambiguous acronym or abbreviation.

Accordingly, the inventors have developed techniques for automatically disambiguating acronyms and abbreviations in extracting facts from medical reports. In some embodiments, a statistical acronym/abbreviation expansion model may be trained to determine the most likely expanded form of an acronym or abbreviation in a medical report based on a training corpus of past medical reports that use the expanded forms. In some embodiments, the most likely expanded form of the acronym or abbreviation may then be input with the medical report to one or more statistical fact extraction models for automatically extracting a clinical fact from the medical report based on the properly expanded acronym/abbreviation. In some embodiments, the extracted clinical fact may correspond to a code from a medical taxonomy (e.g., SNOMED, RxNorm, RadLex, ICD, CPT, E&M, MedDRA, LOINC, NDC, etc.) that may be output from the automatic fact extraction system. The inventors have appreciated that such automated coding of medical reports may be made more accurate in some embodiments (e.g., more accurately corresponding to the intended meaning of the clinician's narration and/or to the true facts of the patient encounter) through such disambiguation of acronyms and abbreviations in the text from which facts corresponding to codes are extracted.

In some embodiments, a linkage may be maintained between each extracted clinical fact and the portion of the free-form narration from which that fact was extracted. For example, if a fact corresponding to "acute myocardial infarction" is extracted from a free-form narration because it included the term "heart attack", a linkage may be maintained between that extracted fact and the words "heart attack" in the free-form narration. In some embodiments, while the clinician or another user is reviewing the extracted clinical facts via a user interface to a fact review system, the system may provide one or more indicators to the user (who may be the clinician himself or a different person) of the different linkages between the different extracted facts and the portions of the free-form narration from which they were extracted. Such indicators may be visual indicators, audio indicators, and/or any other suitable type of indicators, as embodiments are not limited in this respect. In some embodiments, such linkage indicators may enhance the ability of the clinician or other user to review the extracted facts for accuracy, with reference to the specific parts of the free-form narration that generated them. In some embodiments, if a textual representation of the free-form narration has been re-formatted prior to fact extraction, linkages may still be maintained between the extracted facts and the original text narrative, to allow the user to relate the extracted facts to the narration as it was originally given by the clinician. For example, in some embodiments, if an acronym or abbreviation in the free-form narration was automatically expanded for input to the fact extraction component, and a clinical fact was then extracted from text including the expanded form of the acronym or abbreviation, an indicator may be provided of the linkage between the extracted fact and the original, unexpanded acronym or abbreviation in the free-form narration for the user's review. While some embodiments may provide linkage information for each extracted fact, it should be appreciated that some embodiments are not so limited, as linkage information may be provided for one or any subset of the extracted facts.

While a number of inventive features for clinical documentation processes are described above, it should be appreciated that embodiments may include any one of these features, any combination of two or more features, or all of the features, and some embodiments are not limited to any particular number or combination of the above-described features. While some embodiments may address one or more above-discussed shortcomings of traditional methods and/or may provide one or more of the foregoing benefits, it should be appreciated that other embodiments may not provide any of the above-discussed benefits and/or may not address any of the above-discussed deficiencies that the inventors have recognized in conventional techniques. Embodiments can be implemented in any of numerous ways, and are not limited to any particular implementation techniques. Described below are examples of specific implementation techniques; however, it should be appreciate that these examples are provided merely for purposes of illustration, and that other implementations are possible.

One illustrative application for the techniques described herein is for use in a system for enhancing medical documentation processes. An exemplary operating environment for such a system is illustrated in FIG. 1. The exemplary operating environment includes a medical documentation system 100, which may be implemented in any suitable form, as embodiments are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. In some cases of encounters, such as a radiological exam, a clinician may interact with a patient primarily indirectly, by examining images taken of the patient's body, instead of or in addition to being in direct contact with the patient.

One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as embodiments are not limited in this respect.

Another way to provide a free-form narration of the patient encounter may be to verbally speak a dictation of the patient encounter. Such a spoken dictation may be provided in any suitable way, as embodiments are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or to any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as embodiments are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semiautomatically by human editing of a draft transcription produced by ASR. Transcriptions produced by ASR engine 102 and/or by transcriptionist 130 may be encoded or otherwise represented as data in any suitable form, as embodiments are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, embodiments are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as embodiments are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

Any suitable technique(s) for implementing re-formatting, examples of which are described above, may be employed, as embodiments are not limited in this respect. One exemplary technique suitable for performing re-formatting of a text narrative is described in U.S. patent application Ser. No. 11/322,971, filed on Dec. 30, 2005, entitled "Translating Literal Speech to Formatted Text", which is incorporated herein by reference in its entirety. Another exemplary technique that may be used in some embodiments for performing re-formatting of a text narrative involves the use of word N-gram statistical models to predict sentence and/or section boundaries in a text narrative. Such statistical models may be trained on a corpus of documents (e.g., past medical records) with correct punctuation and/or section headings (e.g., supplied by a medical transcriptionist).

In some embodiments, a statistical model may add punctuation (e.g., periods, exclamation points, question marks, etc.) to add one or more sentence boundaries to a text narrative by computing a probability, for each word in the text narrative, that a particular punctuation mark should follow that word. In computing the probability that a word should be followed by a punctuation mark, the statistical model may consider the N-word sequence from the text narrative that ends with that word, and determine the frequency with which that N-word sequence is followed by that punctuation mark in the training data for the statistical model. A lattice may then be constructed using the computed probabilities for all the words in the text narrative, or in a portion of the text narrative, and the best path in terms of combined probability through the lattice may be determined. Where punctuation marks are located in the best path through the lattice, those punctuation marks may be added in those locations to the text narrative in producing the formatted text. In some embodiments, another statistical model may add section headings, corresponding to section boundaries, in a similar fashion. For example, in some embodiments, a statistical model for section headings may compute probabilities, for each word, that the word should be followed by (or preceded by) a section boundary. In some embodiments, in computing probabilities, a statistical model for section headings may consider more words that follow the current word than words that precede the current word. In some embodiments, one or more separate statistical models may be trained to delete incorrect sentence and/or section boundaries. Those models in some embodiments may be trained through feedback from clinician 120 or another user, by observing word sequences (initially including punctuation and/or section boundaries) from which clinician 120 or another user tends to remove the punctuation and/or section boundaries when editing.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used in some embodiments. Exemplary techniques for medical fact extraction are described below.

In some embodiments, a fact extraction component may be implemented using techniques such as those described in U.S. Pat. No. 7,493,253, entitled "Conceptual World Representation Natural Language Understanding System and Method." U.S. Pat. No. 7,493,253 is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology—a concept representing an interruption of blood supply to the heart. Such linkage of multiple medical terms to the same abstract concept in some embodiments may relieve the clinician of the burden of ensuring that only standard medical terms preferred by the institution appear in the free-form narration. For example, in some embodiments, a clinician may be free to use the acronym "AMI" or the colloquial "heart attack" in his free-form narration, and the shared concept linkage may allow the fact extraction component to nevertheless automatically extract a fact corresponding to "acute myocardial infarction".

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as embodiments are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the fact extraction component to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more medical facts from a free-form narration may be used in some embodiments. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as embodiments are not limited in this respect. In addition, a knowledge representation model such as an ontology used by fact extraction component 104 may be constructed in any suitable way, as embodiments are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 104.

As discussed above, it should be appreciated that embodiments are not limited to any particular technique(s) for constructing knowledge representation models. Examples of suitable techniques include those disclosed in the following:

Gómez-Pérez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Large Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

Alternatively or additionally, in some embodiments a fact extraction component may make use of one or more statistical classifier models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as embodiments are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as embodiments are not limited in this respect.

In some embodiments, section membership may be used as a feature of a token. In some embodiments, a section normalization module may be implemented to associate various portions of the narrative text with the proper section(s) to which they should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, radiology reports, progress notes, operative notes, emergency room reports, mental health notes, procedure notes, physical rehabilitation notes, nutritional notes, pathology reports, nursing notes, urgent care notes, office notes, EKG reports, labor & delivery notes, and discharge summaries, as well as many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as embodiments are not limited in this respect. Below are further examples of suitable section headings; however, this list is provided merely for purposes of illustration and is not intended to be limiting or exhaustive:

| | |
|---|---|
| Activities | Active_Problem_List |
| Addendum | Admission_Orders |
| Admitting_Diagnosis | Allergies |
| Anesthesia | Anesthesia_Course |
| Anesthesiologist | Assessment |

-continued

| | |
|---|---|
| Assessment_And_Plan | Assessment_And_Problem_List |
| Assistant | Attending_Physician |
| Chief_Complaint | Code_Status |
| Complications | Condition |
| Consulting_Physician | Date_Of_Admission |
| Date_Of_Discharge | Date_Of_Procedure |
| Date_Of_Service | Description_Of_Procedure |
| Diagnosis | Diet |
| DIFFERENTIAL | Discharge_Activity |
| Discharge_Condition | Discharge_Diagnosis |
| Discharge_Diet | Discharge_Instructions |
| Discharge_Medications | Discharge_Plan |
| Disposition | Drains |
| ED_Course_and_MDM | Emergency_Department_Course |
| Estimated_Blood_Loss | Family_History |
| Fluids | Fluids_Given |
| Follow_Up | History |
| History_And_Physical | History_Of_Present_Illness |
| Hospital_Course | HYPOTHETICAL |
| Imaging | Immunizations |
| Implants | Indications |
| Inserted_Radiology_Note | Instrumentation |
| Laboratory_Data | Location |
| Medical_Decision_Making | Medication_Administered |
| Medications | Medications_And_Allergies |
| Mental_Status | Name_Of_Procedure |
| Objective | Operations_And_Procedure |
| Operative_Conclusion | Operative_Findings |
| Other_Physician | Pathology |
| Past_Medical_History | Past_Surgical_History |
| Physical_Examination | Plan |
| PLANNED | Postoperative_Diagnosis |
| Preoperative_Diagnosis | Present_On_Admission |
| Problem_List | Reason_For_Admission |
| Reason_For_Admission_And_HPI | Reason_For_Consultation |
| Recommendations | Review_Of_Systems |
| Social_History | Specimen_Removed |
| Subjective | Surgeon |
| Transfer_Summary | Urine_Output |
| Vital_Signs | |

A section normalization module may use any suitable technique to associate portions of text with normalized document sections, as embodiments are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N-1) words and/or tokens in the text as a feature of the current token. In another example, affixes (e.g., suffixes such as -ectomy, -oma, -itis, etc.) may be used as features of tokens. In another example, one or more predefined dictionaries (and/or ontologies, etc.) may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as embodiments are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Embodiments are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as embodiments are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis"

feature were hand-labeled with each different entity label in the training corpus. In some embodiments, the probabilities may be normalized such that, for each feature, the probabilities of being associated with each possible entity (fact type) may sum to 1. However, embodiments are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity). In some embodiments, the probabilities learned from the training data for different feature-classification combinations may be stored in an index for later retrieval when applying the learned probabilities to classify an entity in a new input text.

In some embodiments, the statistical entity detection model may be further trained to weight the individual features of a token to determine an overall probability that it should be associated with a particular entity label. For example, if the token "sinusitis" has n extracted features f1 . . . fn having respective probabilities p1 . . . pn of being associated with a "Problem" entity label, the statistical model may be trained to apply respective weights w1 . . . wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as embodiments are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, a probability of an individual token being a particular entity type may be computed by extracting the entity detection model's defined set of features from that token, retrieving the associated probabilities for each entity type for each extracted feature (e.g., as previously computed and stored in an index), and combining the probabilities for all of the features (e.g., applying the entity detection model's defined set of feature weights) to compute a combined probability for each entity type for the token. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as embodiments are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N-1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type. Alternatively or additionally, in some embodiments a relation model may identify two or more different medical facts in a text as having a particular relation to each other, such as a Problem fact being caused by a Social History fact (e.g., pulmonary disease is caused by smoking), or a Problem fact being treated by a Medication fact (e.g., bacterial infection is treated by antibiotic), etc.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as embodiments are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. As further examples, relation annotations for relating two or more facts together may include such annotations as "hasCause," "hasConcurrenceWith," "hasTreatment," and/or any other suitable relation. It should be appreciated, however, that the foregoing are merely examples, and that embodiments are not limited to any particular attributes for any particular fact types. Also, other types of fact relations are possible, including family relative relations, causes-problem relations, improves-problem relations, and many others. Embodiments are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as embodiments are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as embodiments are not limited in this respect. Some standard terms and/or codes may be derived from a government or profession-wide standard taxonomy, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473, and the SNOMED CT concept code for "chronic sinusitis" is 40055000. Any suitable coding system may be used, as embodiments are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes. In some embodiments, the normalization/coding process may assign the appropriate corresponding code(s) from any one or more suitable medical taxonomies to a fact extracted from the medical report text and provide the corresponding code(s) as output.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong, & Yang: "A vector space model for automatic indexing," *Communications of the ACM*, November 1975. This publication is incorporated herein by reference in its entirety. However, these are merely examples, and any suitable technique(s) for normalizing entity tokens to standard terms may be utilized in some embodiments. In some embodiments, a statistical normalization/coding model may be trained to select the most likely term or code from the list of matching terms/codes based on suitably defined features of the text, such as the entity type, the document type, and/or any other suitable features.

In some embodiments, the normalization/coding process may output a single hypothesis for the standard form and/or code corresponding to each extracted fact. For example, the single output hypothesis may correspond to the concept in the ontology (and/or the corresponding code in a medical code taxonomy) linked to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

In some embodiments, as discussed above, accuracy of automated fact extraction and/or coding for a medical report may be improved by disambiguating one or more acronyms and/or abbreviations in the medical report text. This may involve, in some embodiments, identifying an acronym or abbreviation in the medical report that has more than one possible expanded form, and determining which of the possible expanded forms is the most likely phrase for which the acronym or abbreviation stands in that particular instance. For example, the acronym/abbreviation disambiguation process may encounter the initials "RA" in a medical report, and may make a determination as to whether that particular instance of those initials stands for "rheumatoid arthritis," "refractory anemia," "right atrium," "room air," a non-codable entity such as the name of someone whose initials are "RA" (e.g., "Ryan Adams"), or any of the other possible expanded forms of "RA" that could be represented in a medical report.

In some embodiments, matching of an acronym or abbreviation encountered in a medical report to its proper expanded form in that particular instance may be performed by an acronym/abbreviation expansion model, which may be trained statistically in some embodiments using methods similar to those described above for training the statistical entity detection model and/or the statistical relation model. For example, in some embodiments, acronyms and abbreviations in training texts (e.g., past medical reports, and/or any other suitable medical texts) may be manually labeled with their proper expanded forms in each particular context in which they appear. For example, in the training text, "EKG suggests abnormal RA," a human annotator may label the token "RA" with the proper expansion "right atrium" (and may label the token "EKG" with the expansion "electrocardiogram"), while in the context of a different training text, "Patient complains of joint pain from RA," an annotator may label the same token "RA" with the different expansion "rheumatoid arthritis" that represents its proper meaning in that context.

In some embodiments, using techniques similar to those described above for other statistical models and statistical classifier models in general, the labeled training text may be used as input to train the statistical acronym/abbreviation expansion model by extracting features from the text including the acronym or abbreviation, and probabilistically associating the extracted features with the manually supplied label indicating the proper expanded form of the acronym or abbreviation in a particular context. Any suitable set of features may be used, as embodiments are not limited in this respect. In some embodiments, the features for the acronym/abbreviation expansion model may be defined to capture information about the context in which a particular acronym/abbreviation appears. For example, in some embodiments, features used by a statistical acronym/abbreviation model may include the acronym/abbreviation token, the section header (original and/or normalized) of the document section in which the acronym/abbreviation appears (some examples of section headers for medical reports are provided above), the document type (e.g., "work type") of the document in which the acronym/abbreviation appears (some examples of document types for medical reports are provided above), a set of N-gram features including word N-grams in a window of text around the acronym/abbreviation, and/or any other suitable features. In embodiments using N-gram features, any suitable type(s) of N-grams and any suitable window may be used. For example, a window of text from which N-gram features are extracted may be defined as a specified number of words (e.g., 5 words, or any other suitable number of words) preceding and/or following the acronym/abbreviation; the phrase, clause, or sentence including the acronym/abbreviation; a window of a specified number of sentences (e.g., 5 sentences, or any other suitable number of sentences) around the acronym/abbreviation in the text; or any other suitable window specification. Any suitable type(s) of N-grams may be extracted as features, such as unigrams, bigrams, trigrams, and/or any other suitable N-grams. For instance, in one exemplary embodiment, all word unigrams and bigrams within a 5-sentence window (which may or may not be permitted to cross section boundaries, paragraph boundaries, etc.) around an acronym/abbreviation may be extracted as features for the statistical model to disambiguate the acronym/abbreviation to its most likely expanded form. It should be appreciated, however, that the foregoing features are merely exemplary, as some embodiments are not limited to any particular list of features. In some embodiments, classification probabilities for individual features may be pre-computed and stored in an index for efficient retrieval and combination during application of the model.

In some embodiments, alternatively or additionally to collecting manually labeled training data for a statistical acronym/abbreviation expansion model, some or all of the model's training data may be labeled automatically. In some embodiments, a list of all acronyms and abbreviations that the statistical model will be able to recognize, together with all the possible expanded forms of those acronyms and abbreviations from which the statistical model will be able to select, may be assembled, e.g., by a developer of the model. The list may be curated from any suitable source(s) of information about medical acronyms and their possible expansions, some non-limiting examples of which include the SNOMED CT ontology, medical dictionaries, specific institutions' (e.g., hospitals') lists of approved abbreviations, etc. In some embodiments, an automated process may use this curated list of expansions of acronyms and abbreviations to prepare a training corpus for the statistical acronym/abbreviation expansion model, from one or more sets of medical documents such as past medical reports. In some embodiments, the process may search the corpus of texts for all instances of known expansions of known acronyms and abbreviations, and may label each identified instance with its corresponding acronym or abbreviation. For example, given the training text, "EKG suggests abnormal right atrium," the automated labeling process may identify the token "right atrium" as an expanded form of an acronym it its curated list, and may label the token with the corresponding acronym "RA." The automated process may also identify the token "rheumatoid arthritis" as another listed expanded form of the acronym in the training text, "Patient complains of joint pain from rheumatoid arthritis," and may label that token also with the corresponding acronym "RA." In some embodiments, the training corpus automatically labeled in this way may be used to extract features and train the statistical acronym/abbreviation expansion model in the same way as if the identified tokens had been the acronyms/abbreviations labeled with their proper expansions. In some embodiments, this may be facilitated by replacing identified expansion tokens in the training data with their corresponding acronyms or abbreviations, and then labeling the replacement acronyms/abbreviations with the expanded forms that they replaced.

Once the statistical acronym/abbreviation expansion model is trained (whether using manually labeled or automatically labeled training data, or both), in some embodiments it may be applied in the processing of new medical reports to identify and expand any known acronyms and abbreviations (e.g., those that are in the curated list) in the medical reports. In some embodiments, upon identifying an acronym or abbreviation in a medical report, the model may compute, for each of multiple phrases (which may be single- and/or multiple-word phrases) that are possible expanded forms of the acronym or abbreviation, a probability (based on extracted contextual features) that the respective phrase is the proper expanded form for the acronym/abbreviation in that particular context. The model may then select the most likely expanded form as the phrase having the highest computed probability, and may label the acronym/abbreviation in the medical report with the selected most likely expanded form for further processing by the medical documentation system. In some embodiments, the model may also output a confidence score, e.g., based on the computed probability. In some embodiments, rather than outputting only the best (e.g., most probable) hypothesis for a particular acronym/abbreviation's expanded form, the statistical acronym/abbreviation expansion model may output a list of multiple alternative hypotheses, e.g., with corresponding probabilities, for the expansion. In some embodiments, as discussed further below, the statistical acronym/abbreviation expansion model may also consider whether a particular acronym/abbreviation occurs in a context in which it represents a non-codable entity (e.g., a non-medical context), such that no clinical fact should be extracted based on that acronym/abbreviation.

In some embodiments, the acronym/abbreviation expansion model may be applied to the text of a medical report, e.g., by fact extraction component 104 or a different component, before the application of one or more other models and/or processes, such that the determined expanded forms of the acronyms/abbreviations may be used as input to subsequent processing. For example, in some embodiments, acronym/abbreviation expansion may be performed after section normalization, and before entity detection is performed on the text. In some such embodiments, the expanded forms of the acronyms/abbreviations (and, in some embodiments, the corresponding computed probabilities and/or confidence scores) may be used as features by the entity detection model to enhance the accuracy of the entity detection. In some embodiments, acronym/abbreviation expansion may be performed before normalization/coding, either before or after entity detection and/or relation modeling. In some such embodiments, the proper expanded form of an acronym or abbreviation may be input to the normalization/coding process and matched to one or more terms in an ontology and/or codes in a medical taxonomy. In some embodiments, multiple alternative hypotheses for the proper expanded form of an acronym/abbreviation may each be matched to one or more terms and/or codes to generate multiple alternative hypotheses for proper terms and/or codes for the extracted medical fact, with corresponding probabilities and/or scores. In some embodiments, if the probability and/or score computed by the acronym/abbreviation expansion model for the expanded form of an acronym/abbreviation is below a specified threshold, then the acronym/abbreviation itself, rather than the determined expanded form, may be used as input to subsequent processing such as entity detection and/or normalization/coding.

In some cases, the inventors have recognized that some instances of an acronym or abbreviation should not be expanded to a known expanded form that has a medical sense, even though that acronym or abbreviation may be represented in the curated list as corresponding to those medical expanded forms. For example, the initials "MS" may be represented in a curated list of medical expansions as having the possible expanded forms "multiple sclerosis," "musculoskeletal," and "milliseconds." However, in some instances, the initials "MS" in a particular medical report context may not stand for any of these possible expanded forms from the list, but rather may stand for something non-codable, such as the initials of someone's name, as in the text, "Electronically signed by MS" ("Michael Smith"). Accordingly, in some embodiments, a statistical acronym/abbreviation expansion model may be trained to consider an additional possible class for each acronym/abbreviation, in which the acronym/abbreviation stands for a non-codable entity.

In some embodiments, training data for allowing the statistical classifier to learn the feature distributions of the non-codable entity classes may be provided using user corrections to previously coded medical reports in which false positives were noted. For example, in a past medical report, fact extraction component 104 may have mistakenly extracted a fact corresponding to the diagnosis "multiple sclerosis" from the instance of "MS" in the text, "Electronically signed by MS." In this case, a user may correct the inaccurate fact extraction (e.g., using fact review techniques such as those described below) by noting that the extracted diagnosis fact was a false positive and in fact should not have been extracted from this instance of "MS" (which in actuality here stands for a clinician's name and not a diagnosis). In some embodiments, texts with corrections such as these may be used as labeled training data for learning the probability distributions of features of particular acronyms/abbreviations when they represent non-codable entities from which clinical facts such as codes should not be extracted. Then, in some embodiments, the statistical acronym/abbreviation expansion model may use the non-codable entity class as an additional possible expansion label for the corresponding acronym/abbreviation, such that the acronym/abbreviation may be labeled by the model as a non-codable entity if that is the most likely classification of its expanded form. Thus, for example, a statistical acronym/abbreviation expansion classifier that encounters the initials "MS" in a medical report may compute probabilities for the possible expansions "multiple sclerosis," "musculoskeletal," "milliseconds," and "[non-codable entity] MS," and may select the highest-probability of these expansion classes to label the instance of the initials. In some embodiments, when an acronym/abbreviation is labeled as a non-codable entity by the acronym/abbreviation expansion model, that label may be provided as a feature to subsequent models (e.g., entity detection and/or normalization/coding models), and a result may be suppression of the extraction of any clinical fact from the acronym/abbreviation. For example, in some embodiments, a statistical entity detection model may use the codable/non-codable feature of an instance of an acronym/abbreviation to determine whether or not to identify the acronym/abbreviation token as a mention of an entity of a known medical type.

It should be appreciated that the foregoing are merely examples, and that fact extraction component 104 may be implemented in any suitable way and/or form in some embodiments.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as embodiments are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as embodiments are not limited to any particular distribution of local and/or remote processing capabilities.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, and/or any other suitable input form, as embodiments are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once automatically extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input, and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3B:
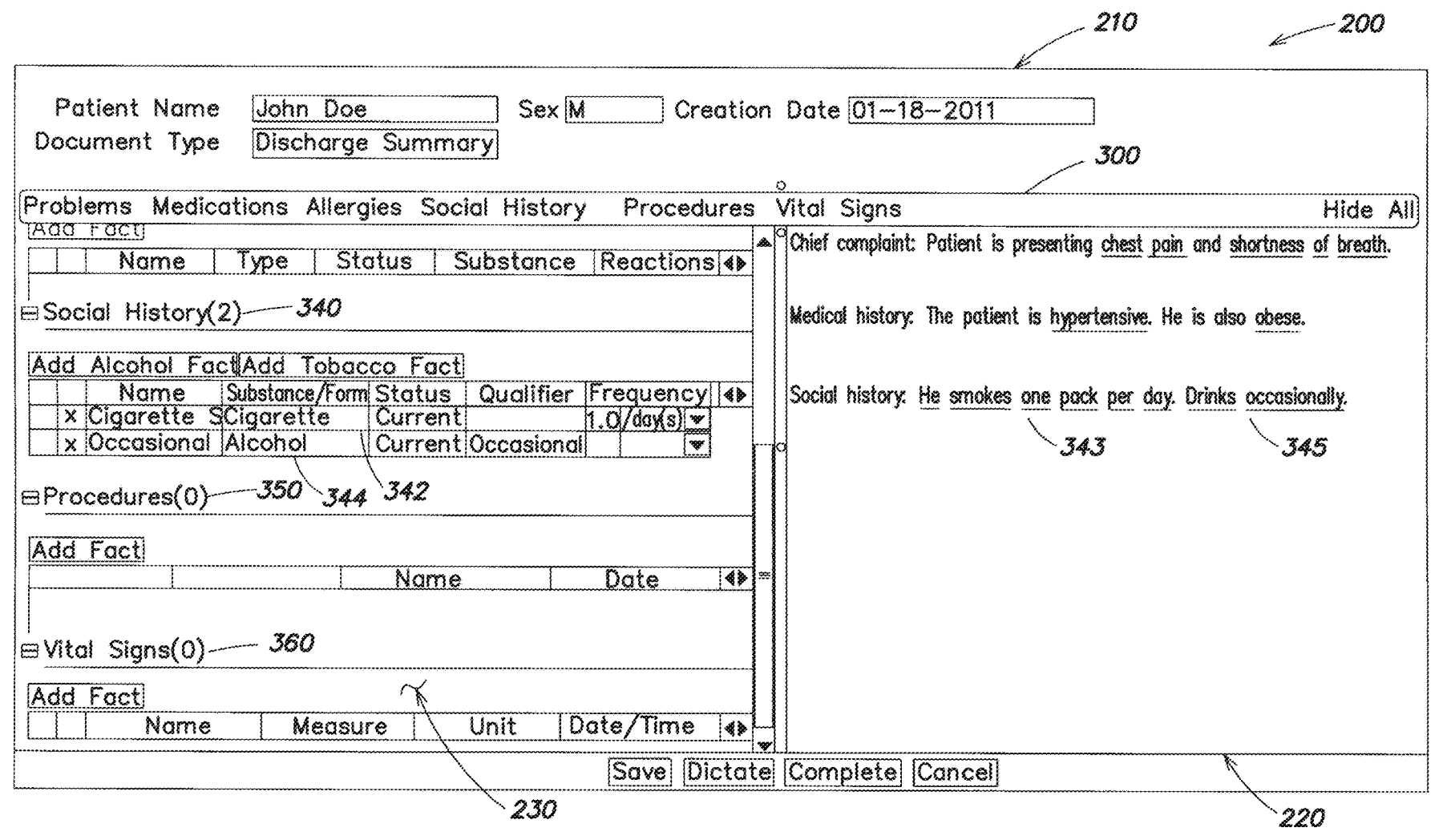

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as embodiments are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. In the example depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as embodiments are not limited to any particular organizational system for facts, fact categories and/or fact components.

Exemplary List of Fact Categories and Component Fields

Category: Problems. Fields: Name, SNOMED status, ICD code.

Category: Medications. Fields: Name, Status, Dose form, Frequency, Measures, RxNorm code, Administration condition, Application duration, Dose route.

Category: Allergies. Fields: Allergen name, Type, Status, SNOMED code, Allergic reaction, Allergen RxNorm.

Category: Social history—Tobacco use. Fields: Name, Substance, Form, Status, Qualifier, Frequency, Duration, Quantity, Unit type, Duration measure, Occurrence, SNOMED code, Norm value, Value.

Category: Social history—Alcohol use. Fields: Name, Substance, Form, Status, Qualifier, Frequency, Duration, Quantity, Quantifier, Unit type, Duration measure, Occurrence, SNOMED code, Norm value, Value.

Category: Procedures. Fields: Name, Date, SNOMED code.

Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Embodiments are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as embodiments are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

Figure 4:
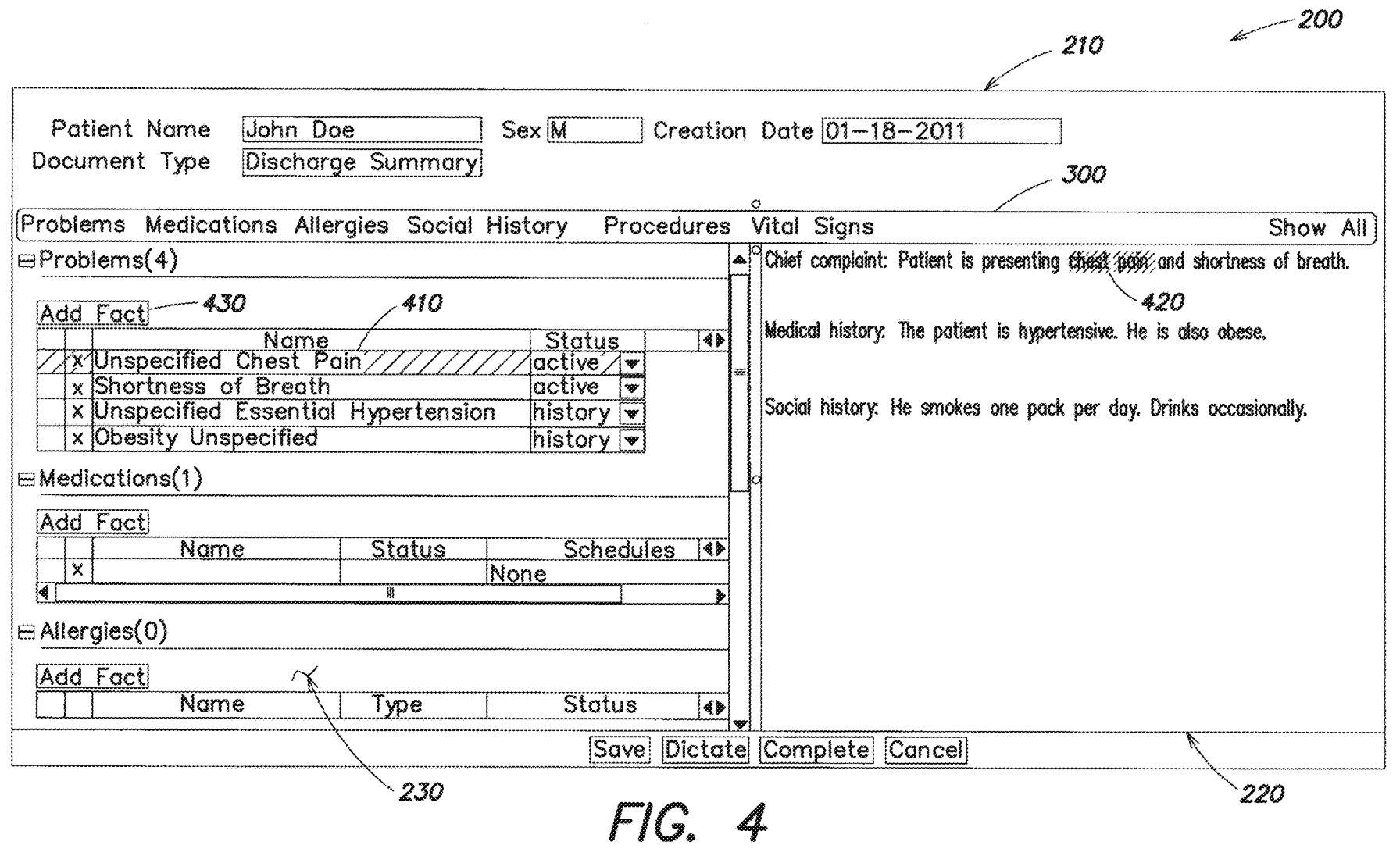

In some embodiments, GUI 200 may be configured to allow the user to select one or more of the medical facts in fact panel 230, and in response to the selection, may provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as embodiments are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as embodiments are not limited in this respect. In addition, embodiments are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as embodiments are not limited in this respect.

In some embodiments, GUI 200 may be configured to present to the user multiple alternative hypotheses for a medical fact to be extracted from the text narrative. This may be done in any suitable way, as embodiments are not limited in this respect. As described above, in some embodiments, alternative hypotheses may be generated by fact extraction component 104 through processing of the text narrative by one or more statistical fact extraction models. In some embodiments, each statistical model or model component applied may generate a list of alternative hypotheses for its output, and fact extraction component 104 may compile an N-best list of all of the combined alternative hypotheses using any suitable thresholding technique. For example, in some embodiments, an acronym/abbreviation expansion model may generate multiple alternative hypotheses, each of which may be processed by an entity detection model to generate multiple alternative hypotheses, each of which may be processed by a relation model to generate multiple alternative hypotheses, each of which may be processed by a normalization/coding stage to generate multiple alternative hypotheses, and so on. In other embodiments, not all stages of fact extraction component 104 may output alternative hypotheses, but one or more particular processing stages of fact extraction may be selected (e.g., by one or more developers of fact extraction component 104) to generate alternative hypotheses to be carried through subsequent processing stages. It should be appreciated, however, that the foregoing are merely examples, and any suitable technique for generating multiple alternative hypotheses for a fact to be extracted may be used, as embodiments are not limited in this respect.

In some embodiments, each of the alternative hypotheses output by fact extraction component 104 may represent a different semantic meaning, and only one of the alternative hypotheses may accurately represent the intended semantic meaning of the portion of the text narrative from which the alternative hypotheses were extracted. For example, consider the text, "She has acute sinusitis; chronic attacks of asthma may be a factor." In some embodiments, fact extraction component 104 may output "sinusitis," "sinusitis, acute," and "sinusitis, chronic" as alternative hypotheses for the intended semantic meaning of the text portion "acute sinusitis; chronic." In this case, only "sinusitis, acute" accurately represents the intended semantic meaning of the text. "Sinusitis, chronic" is incorrect because the text was not intended to indicate that the sinusitis is chronic, and "sinusitis" is inaccurate because the text was intended to indicate a more specific fact: that the sinusitis is acute. This example also illustrates that in some embodiments one of the alternative hypotheses may be a parent concept of another of the alternative hypotheses. In this example, "sinusitis" is a parent concept of "sinusitis, acute," as "sinusitis, acute" is a more specific type of "sinusitis." In formal semantic terms, the child concept shares all characteristics of the parent concept, and also has one or more additional characteristics (in this case, that of being "acute").

It should be appreciated that techniques described herein may in many cases provide significantly more functionality than simply identifying keywords in a narrative and mapping those keywords to standard codes such as billing codes (e.g., ICD codes). Extracting underlying semantic meanings (e.g., the medical facts being expressed by the narrative) may in many cases allow for more complex understanding of relationships between narrative expressions and the codes they produce. For example, in many cases, there may not be a simple one-to-one relationship between text and codes, or between extracted facts and codes. In some embodiments, two or more of the alternative hypotheses for a particular medical fact (only one of which may accurately represent the intended semantic meaning of the corresponding text) may correspond to the same billing code. For example, if a set of alternative fact hypotheses included "shoulder bursitis," "right shoulder bursitis," and "severe right shoulder bursitis," all three of those alternative hypotheses (each representing a different fact) would correspond to the same ICD9 billing code 726.10, "Disorders of bursae and tendons in shoulder region, unspecified." In some embodiments, one or more alternative hypotheses may not correspond to any billing code at all. For example, hypotheses for Problem and Procedure fact types may often correspond to billing codes, but hypotheses for other fact types such as Allergy fact types, Social History fact types, Vital Signs fact types, etc., often do not correspond to any billing codes. In some examples, alternative hypotheses for a particular medical fact that correspond to the same billing code may correspond to different codes from a more detailed medical taxonomy, such as the SNOMED CT taxonomy. Similarly, in some embodiments some medical facts may be extracted that do not correspond to any billing code, but may be coded using a more detailed medical taxonomy not directly used for billing.

In some embodiments, GUI 200 may be configured to provide any of various ways for multiple alternative hypotheses for a medical fact to be presented to the user. Examples are provided below; however, it should be appreciated that any suitable technique or combination of techniques for presenting alternative hypotheses may be used, as embodiments are not limited in this respect. In one example, the user may select (e.g., using any suitable selection technique, examples of which are provided above) a portion of the text narrative in text panel 220, and GUI 200 may be configured to provide a list of alternative hypotheses for the medical fact to be extracted from that portion of the text narrative, e.g., in fact panel 230, in response to the user selection of the portion of the text narrative. In another example, GUI 200 may be configured to initially present one of the alternative hypotheses (e.g., the hypothesis with the greatest calculated likelihood of accurately representing the intended semantic meaning of the portion of the text narrative) in fact panel 230. In response to a user selection of the presented fact hypothesis, GUI 200 may then present a list of the other alternative hypotheses for the selected fact.

In some embodiments, GUI 200 may be configured to allow the user, once the list of alternative hypotheses has been presented, to select one of the hypotheses from the list. In response to the user selection, in some embodiments system 100, e.g., via fact review component 106, may designate the selected hypothesis as accurately representing the semantic meaning of the portion of the text from which it was extracted. In some embodiments, this may involve updating the list of facts displayed in fact panel 230 to confirm the selected hypothesis as the finalized extracted fact corresponding to that portion of the text narrative.

In some embodiments, GUI 200 may be configured to provide any of various ways for the user to make one or more changes to the set of medical facts extracted from the text narrative by fact extraction component 104 and displayed in fact panel 230. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu; other techniques for allowing editing of the status field are also possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

Figure 5:
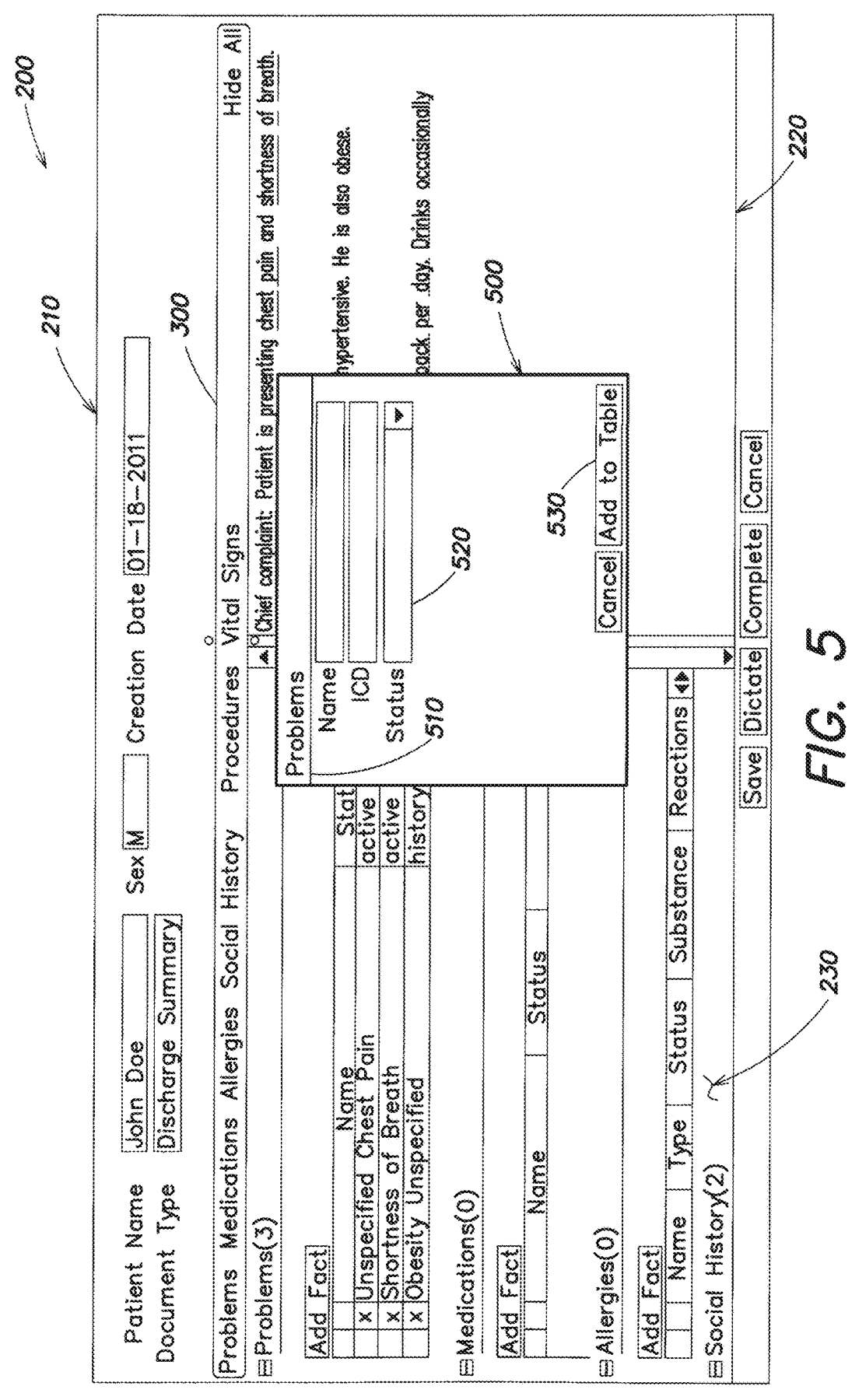

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as embodiments are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as embodiments are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

In some embodiments, clinical facts extracted automatically from a text narrative by fact extraction component 104 may be reviewed and/or edited by a user 150 other than the clinician 120 who provided the text narrative. For example, in some embodiments user 150 may be a coding specialist who is assigned the task of reviewing and editing the set of clinical facts (which may include billing codes and/or other medical taxonomy codes) into a version fit to be incorporated into an electronic medical record, patient reports, order forms, or other document types. In such a "back-end" arrangement, the set of clinical facts settled upon by coding specialist 150 may then in some embodiments be transmitted to clinician 120 to give final approval to the set of facts. In some other embodiments, coding specialist 150 may not be required. For example, in a "front-end" arrangement, clinician 120 may review and possibly edit the set of clinical facts himself, and finally approve the set of facts when he is satisfied. This may occur during the patient encounter in some embodiments, or at some time thereafter (e.g., before clinician 120 finally approves or signs off on the report) in other embodiments.

In some embodiments, one or more of the facts in the set collected (either by fact extraction from a text narrative or by direct entry as one or more discrete structured data items) from the patent encounter may correspond to one or more standard codes used for billing, ordering, evaluating quality of care, or the like. Such standard codes may be specific to the healthcare institution or may be a standard shared by multiple institutions. Examples of such standard coding systems include, but are not limited to, ICD codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes. Some such standard coding systems are hierarchical, in that certain codes within the system are more specific versions of other codes within the system. For example, in the ICD-10 coding system, code I20 represents "angina pectoris" (chest pain due to lack of blood and oxygen to the heart muscle). More specific versions of ICD-10 code I20 include I20.0 ("unstable angina"), I20.1 ("angina pectoris with documented spasm"), I20.8 ("other forms of angina pectoris") and I20.9 ("angina pectoris, unspecified").

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. The electronic medical record may be stored as computer-readable data in any suitable format, e.g., in a data store 160. In some embodiments, clinician 120 and/or coding specialist (or other user) 150 may finally approve the set of medical facts before they are included in any patient record; however, embodiments are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

It should be appreciated from the foregoing that one embodiment is directed to a method 600 for coding a medical report. Method 600 may be performed, for example, by one or more components of a medical documentation system such as fact extraction component 104, although other implementations are possible, as method 600 is not limited in this respect. Method 600 begins at act 610, at which an acronym or abbreviation may be identified in a medical report. As discussed above, this may be done, in some embodiments, by searching the medical report for any tokens matching acronyms or abbreviations in a curated list of known acronyms and abbreviations. At act 620, a plurality of phrases that are possible expanded forms of the identified acronym or abbreviation (and that are not explicitly included in the medical report, since the acronym/abbreviation has been used instead) may be identified. As discussed above, this may be done, in some embodiments, by looking up the known possible expanded forms of the identified acronym/abbreviation in the curated list of acronyms/abbreviations and their known expanded forms.

At act 630, a most likely expanded form of the acronym/abbreviation may be selected from the plurality of phrases representing the known possible expanded forms of the acronym/abbreviation. As discussed above, this may be done, in some embodiments, by applying to the medical report a statistical acronym/abbreviation expansion model that has been trained on a corpus of medical reports. Exemplary techniques for configuring and training such a statistical model are described above. As discussed above, in some embodiments, applying the statistical acronym/abbreviation expansion model to the medical report may include extracting suitably defined features from the medical report text and inputting those features to a statistical acronym/abbreviation expansion classifier to compute from the features probabilities that the acronym/abbreviation stands for various possible expanded forms. In some embodiments, as discussed above, features for the statistical acronym/abbreviation expansion model may be defined to capture information about the context in which the instance of the acronym/abbreviation occurs. In some embodiments, applying the statistical acronym/abbreviation expansion model to the medical report may include extracting unigrams and bigrams from a specified window of text around the acronym or abbreviation in the medical report and inputting the extracted unigrams and bigrams as features to a statistical acronym/abbreviation expansion classifier. In some embodiments, applying the statistical acronym/abbreviation expansion model to the medical report may include extracting a section header of a section including the acronym or abbreviation in the medical report and inputting the extracted section header as a feature to a statistical acronym/abbreviation expansion classifier. In some embodiments, applying the statistical acronym/abbreviation expansion model to the medical report may include identifying a document type of the medical report and inputting the identified document type as a feature to a statistical acronym/abbreviation expansion classifier.

At act 640, a clinical fact may be extracted from the medical report based at least in part on the most likely expanded form of the acronym or abbreviation determined at act 630. As discussed above, this may be done, in some embodiments, by applying to the medical report (with the expanded acronym or abbreviation labeled or otherwise included with the medical report) one or more statistical fact extraction models. These may include, for example, a statistical entity detection model and/or a relation model, in some embodiments, as discussed above. Exemplary techniques for configuring and training such statistical model(s) are described above. At act 650, a corresponding code from a medical taxonomy may be assigned to the extracted clinical fact from the medical report, e.g., by a normalization/coding process. Exemplary techniques for implementing such a coding process are described above. In some embodiments, the code (or multiple corresponding codes) may be a code from a medical taxonomy such as SNOMED, RxNorm, RadLex, ICD, CPT, E&M, MedDRA, LOINC, and/or NDC, that corresponds to the phrase determined to be the most likely expanded form of the acronym/abbreviation in the medical report.

In some embodiments, as discussed above, at least one of the possible expanded forms for an acronym/abbreviation considered by the statistical acronym/abbreviation expansion model may be designated a non-codable entity. In some embodiments, as discussed above, the statistical acronym/abbreviation expansion model may be trained to recognize text contexts in which a particular acronym/abbreviation stands for a non-codable entity based on false positives noted in user corrections to previously coded medical reports. In some embodiments, in response to selecting a non-codable entity as the most likely expansion of an acronym/abbreviation in a medical report by application of the statistical acronym/abbreviation expansion model, an automated fact extraction system may suppress extraction of any clinical fact from a portion of text around (including) that instance of the acronym/abbreviation in the medical report.

Figure 7:
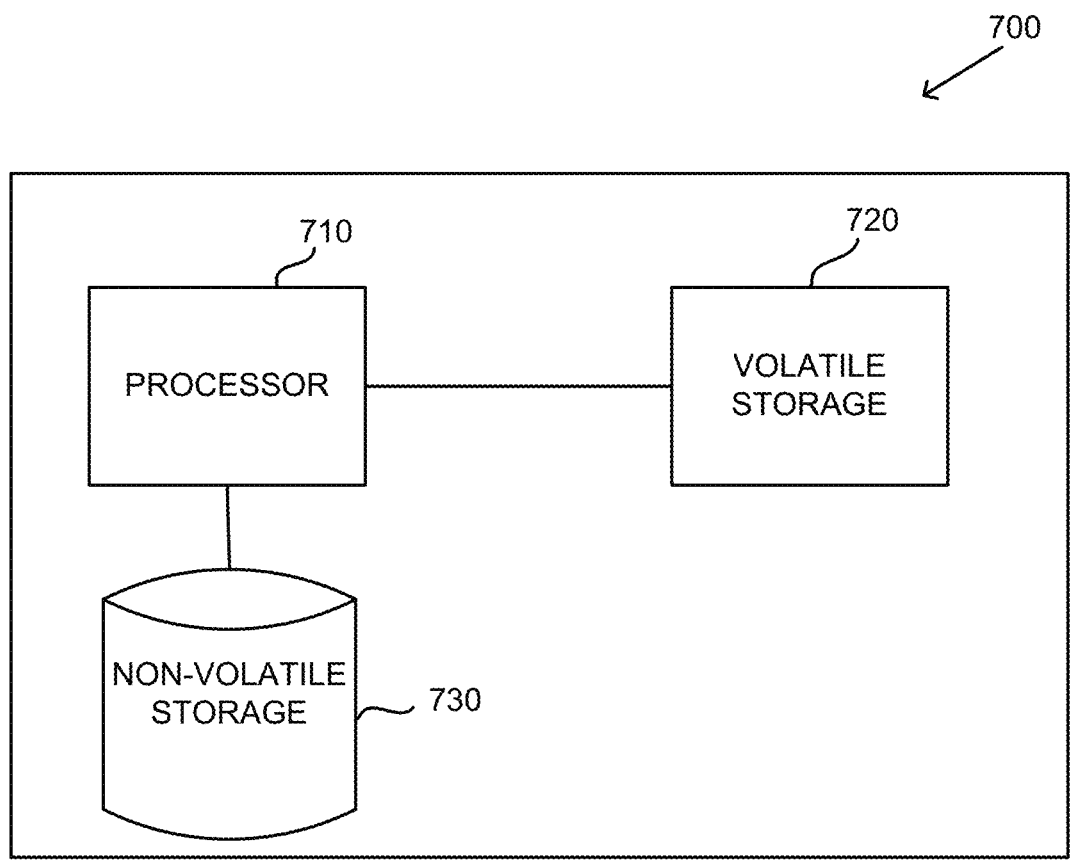
FIG. 7 is a block diagram of an exemplary computer system on which some embodiments may be implemented.

A medical documentation system in accordance with the techniques described herein may take any suitable form, as embodiments are not limited in this respect. An illustrative implementation of a computer system 700 that may be used in connection with some embodiments is shown in FIG. 7. One or more computer systems such as computer system 700 may be used to implement any of the functionality described above. The computer system 700 may include one or more processors 710 and one or more computer-readable storage media (i.e., tangible, non-transitory computer-readable media), e.g., volatile storage 720 and one or more non-volatile storage media 730, which may be formed of any suitable non-volatile data storage media. The processor 710 may control writing data to and reading data from the volatile storage 720 and the non-volatile storage device 730 in any suitable manner, as embodiments are not limited in this respect. To perform any of the functionality described herein, the processor 710 may execute one or more instructions stored in one or more computer-readable storage media (e.g., volatile storage 720), which may serve as tangible, non-transitory computer-readable media storing instructions for execution by the processor 710.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with one or more processors programmed using microcode or software to perform the functions recited above.

In this respect, it should be appreciated that one implementation comprises at least one computer-readable storage medium (i.e., a tangible, non-transitory computer-readable medium, such as a computer memory (e.g., hard drive, flash memory, processor working memory, etc.), a floppy disk, an optical disk, a magnetic tape, or other tangible, non-transitory computer-readable medium) encoded with a computer program (i.e., a plurality of instructions), which, when executed on one or more processors, performs above-discussed functions. The computer-readable storage medium can be transportable such that the program stored thereon can be loaded onto any computer resource to implement functionality discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-discussed functionality.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method comprising:
analyzing free-form input regarding an encounter with a patient by a clinician with at least one processor to determine at least one clinical fact expressed in the free-form input, wherein the analyzing comprises analyzing the free-form input using the at least one processor and at least one statistical model to determine the at least one clinical fact, the at least one statistical model having been trained on a corpus of medical text to identify clinical facts expressed within input to the at least one statistical model, wherein analyzing the free-form input using the at least one processor and the at least one statistical model comprises:
selecting with the at least one statistical model, for a sequence of initials in the free-form input and from among a plurality of phrases that are not explicitly included in the free-form input and that are different expanded forms of the sequence of initials in the free-form input, a phrase that is likely to be an intended expanded form of the sequence of initials in the free-form input; and
analyzing the free-form input and the phrase, of the plurality of phrases, not included in the free-form input but determined by the at least one statistical model as likely to be the intended expanded form of the sequence of initials, to determine the at least one clinical fact expressed in the free-form input, wherein the analyzing comprises:
when the phrase determined by the at least one statistical model as likely to be the intended expanded form corresponds to a non-codable entity, refraining from extracting a clinical fact from a portion of the free-form input that includes the sequence of initials, and
when the phrase determined by the at least one statistical model as likely to be the intended expanded form does not correspond to a non-codable entity, extracting a clinical fact from a portion of the free-form input based at least in part on processing the phrase not included in the free-form input with the at least one statistical model implemented by the at least one processor.

2. The method of claim 1, further comprising assigning a corresponding medical taxonomy code to the extracted clinical fact from the free-form input.

3. The method of claim 1, wherein selecting with the at least one statistical model a phrase that is likely to be an intended expanded form of the sequence of initials in the free-form input comprises:
applying to the free-form input a statistical expansion model implemented by the at least one processor executing stored instructions and trained on a corpus of medical input to determine likely intended expanded forms of sequences of initials processed with the statistical expansion model.

4. The method of claim 1, wherein processing the free-form input using the at least one processor and the at least one statistical model comprises:
extracting unigrams and bigrams from a specified window of text around the sequence of initials in the free-form input; and
analyzing the extracted unigrams and bigrams as features using the at least one statistical model.

5. The method of claim 1, wherein processing the free-form input using the at least one processor and the at least one statistical model comprises:
extracting a section header of a section including the sequence of initials in the free-form input; and
analyzing the extracted section header as a feature using the at least one statistical model.

6. The method of claim 1, wherein processing the free-form input using the at least one processor and the at least one statistical model comprises:
identifying a document type of the free-form input; and
analyzing the identified document type as a feature using the at least one statistical model.

7. A system comprising:
at least one processor; and
at least one storage medium storing processor-executable instructions that, when executed by the at least one processor, perform a method comprising:
analyzing free-form input regarding an encounter with a patient by a clinician with at least one processor to determine at least one clinical fact expressed in the free-form input, wherein the analyzing comprises analyzing the free-form input using the at least one processor and at least one statistical model to determine the at least one clinical fact, the at least one statistical model having been trained on a corpus of medical text to identify clinical facts expressed within input to the at least one statistical model, wherein analyzing the free-form input using the at least one processor and the at least one statistical model comprises:
selecting with the at least one statistical model, for a sequence of initials in the free-form input and from among a plurality of phrases that are not explicitly included in the free-form input and that are different expanded forms of the sequence of initials in the free-form input, a phrase that is likely to be an intended expanded form of the sequence of initials in the free-form input; and
analyzing the free-form input and the phrase, of the plurality of phrases, not included in the free-form input but determined by the at least one statistical model as likely to be the intended expanded form of the sequence of initials, to determine the at least one clinical fact expressed in the free-form input, wherein the analyzing comprises:
when the phrase determined by the at least one statistical model as likely to be the intended expanded form corresponds to a non-codable entity, refraining from extracting a clinical fact from a portion of the free-form input that includes the sequence of initials, and when the phrase determined by the at least one statistical model as likely to be the intended expanded form does not correspond to a non-codable entity, extracting a clinical fact based at least in part on processing the phrase not included in the free-form input with the at least one statistical model implemented by the at least one processor.

8. The system of claim 7, further comprising assigning a corresponding medical taxonomy code to the extracted clinical fact from the free-form input.

9. The system of claim 7, wherein selecting with the at least one statistical model a phrase that is likely to be an intended expanded form of the sequence of initials in the free-form input comprises:

applying to the free-form input a statistical expansion model implemented by the at least one processor executing stored instructions and trained on a corpus of medical input to determine likely intended expanded forms of sequences of initials processed with the statistical expansion model.

10. The system of claim 7, wherein processing the free-form input using the at least one processor and the at least one statistical model comprises:

extracting unigrams and bigrams from a specified window of text around the sequence of initials in the free-form input; and analyzing the extracted unigrams and bigrams as features using the at least one statistical model.

11. The system of claim 7, wherein processing the free-form input using the at least one processor and the at least one statistical model comprises:

extracting a section header of a section including the sequence of initials in the free-form input; and analyzing the extracted section header as a feature using the at least one statistical model.

12. The system of claim 7, wherein processing the free-form input using the at least one processor and the at least one statistical model comprises:

identifying a document type of the free-form input; and analyzing the identified document type as a feature using the at least one statistical model.

13. At least one non-transitory computer-readable storage medium storing computer-executable instructions that, when executed, perform a method comprising:

analyzing free-form input regarding an encounter with a patient by a clinician with at least one processor to determine at least one clinical fact expressed in the free-form input, wherein the analyzing comprises analyzing the free-form input using the at least one processor and at least one statistical model to determine the at least one clinical fact, the at least one statistical model having been trained on a corpus of medical text to identify clinical facts expressed within input to the at least one statistical model, wherein analyzing the free-form input using the at least one processor and the at least one statistical model comprises:

selecting with the at least one statistical model, for a sequence of initials in the free-form input and from among a plurality of phrases that are not explicitly included in the free-form input and that are different expanded forms of the sequence of initials in the free-form input, a phrase that is likely to be an intended expanded form of the sequence of initials in the free-form input; and analyzing the free-form input and the phrase, of the plurality of phrases, not included in the free-form input but determined by the at least one statistical model as likely to be the intended expanded form of the sequence of initials, to determine the at least one clinical fact expressed in the free-form input, wherein the analyzing comprises:

when the phrase determined by the at least one statistical model as likely to be the intended expanded form corresponds to a non-codable entity, refraining from extracting a clinical fact from a portion of the free-form input that includes the sequence of initials, and when the phrase designated determined by the at least one statistical model as likely to be the intended expanded form does not correspond to a non-codable entity, extracting a clinical fact based at least in part on processing the phrase not included in the free-form input with the at least one statistical model implemented by the at least one processor.

14. The computer-readable storage medium of claim 13, further comprising assigning a corresponding medical taxonomy code to the extracted clinical fact from the medical report.

15. The computer-readable storage medium of claim 13, wherein selecting with the at least one statistical model a phrase that is likely to be an intended expanded form of the sequence of initials in the free-form input comprises:

applying to the free-form input a statistical expansion model implemented by the at least one processor executing stored instructions and trained on a corpus of medical input to determine likely intended expanded forms of sequences of initials processed with the statistical expansion model.

16. The computer-readable storage medium of claim 13, wherein processing the free-form input using the at least one processor and the at least one statistical model comprises:

extracting unigrams and bigrams from a specified window of text around the sequence of initials in the free-form input; and analyzing the extracted unigrams and bigrams as features using the at least one statistical model.

17. The computer-readable storage medium of claim 13, wherein processing the free-form input using the at least one processor and the at least one statistical model comprises:

extracting a section header of a section including the sequence of initials in the free-form input; and analyzing the extracted section header as a feature using the at least one statistical model.

18. The method of claim 1, wherein:

selecting the phrase that is likely to be an intended expanded form of the sequence of initials, from among the plurality of phrases that are different expanded forms of the sequence of initials, comprises:

analyzing the sequence of initials and at least a portion of the free-form input using the at least one statistical model and generating one or more confidence scores for each of the plurality of phrases, and selecting, from the plurality of phrases, the phrase that is likely to be the intended expanded form of the sequence of initials in the free-form input based at least in part on the one or more confidence scores for each of the plurality of phrases, the phrase that is likely to be the intended expanded form being one of the plurality of phrases.

19. The system of claim 7, wherein:
selecting the phrase that is likely to be an intended expanded form of the sequence of initials, from among the plurality of phrases that are different expanded forms of the sequence of initials, comprises:
analyzing the sequence of initials and at least a portion of the free-form input using the at least one statistical model and generating one or more confidence scores for each of the plurality of phrases, and
selecting, from the plurality of phrases, the phrase that is likely to be the intended expanded form of the sequence of initials in the free-form input based at least in part on the one or more confidence scores for each of the plurality of phrases, the phrase that is likely to be the intended expanded form being one of the plurality of phrases.

20. The computer-readable storage medium of claim 13, wherein:
selecting the phrase that is likely to be an intended expanded form of the sequence of initials, from among the plurality of phrases that are different expanded forms of the sequence of initials, comprises:
analyzing the sequence of initials and at least a portion of the free-form input using the at least one statistical model and generating one or more confidence scores for each of the plurality of phrases, and
selecting, from the plurality of phrases, the phrase that is likely to be the intended expanded form of the sequence of initials in the free-form input based at least in part on the one or more confidence scores for each of the plurality of phrases, the phrase that is likely to be the intended expanded form being one of the plurality of phrases.

21. The method of claim 1, further comprising training the at least one statistical model to recognize text contexts in which the sequence of initials stands for the non-codable entity, based on false positives noted in user corrections to previously coded medical reports.

22. The method of claim 2, wherein assigning the corresponding medical taxonomy code to the extracted clinical fact comprises identifying a code, from a medical taxonomy selected from the group consisting of SNOMED, RxNorm, RadLex, ICD, CPT, E&M, MedDRA, LOINC, and NDC taxonomies of codes, corresponding to the phrase that is likely to be the intended expanded form of the sequence of initials in the free-form input.

* * * * *